United States Patent [19]

Raasch

[11] 3,947,511

[45] Mar. 30, 1976

[54] 1-HYDROCARBYL-3-MONO- AND -DITHIOCARBAMOYLUREAS

[75] Inventor: Maynard S. Raasch, Wilmington, Del.

[73] Assignee: E. I. Du Pont de Nemours and Company, Wilmington, Del.

[22] Filed: Nov. 25, 1970

[21] Appl. No.: 92,951

[52] U.S. Cl.............. 260/545 R; 71/88; 71/94; 71/95; 71/100; 260/239 BF; 260/246 B; 260/293.63; 260/293.64; 260/293.73; 260/293.85; 260/326.25; 260/326.4; 260/814; 260/247.1 R; 260/247.1 T
[51] Int. Cl.$^2$............. C07C 155/04; C07C 155/09
[58] Field of Search....... 260/240 R, 247.1, 239 BF, 260/293.73, 293.85, 326.3, 545 R, 293.63, 293.64, 326.25

[56] References Cited
UNITED STATES PATENTS

| | | | |
|---|---|---|---|
| 3,234,275 | 2/1966 | Malz et al. | 260/552 |
| 3,356,484 | 12/1967 | Richter | 71/87 |
| 3,359,301 | 12/1967 | Speziale et al. | 260/471 |
| 3,404,975 | 10/1968 | Wilson et al. | 71/100 |
| 3,439,018 | 4/1969 | Brookes et al. | 260/471 |
| 3,493,360 | 2/1970 | Fancher et al. | 71/100 |
| 3,525,765 | 8/1970 | Fancher et al. | 260/479 |
| 3,621,055 | 11/1971 | Fischer et al. | 260/545 R |

OTHER PUBLICATIONS

Kurzer, J. Chem. Soc. 549, 3360–3366, (1953).

*Primary Examiner*—G. Thomas Todd

[57] ABSTRACT

Novel 1-hydrocarbyl-3-(thiocarbamoylthio)ureas and 1-hydrocarbyl-3-(carbamoylthio)ureas are prepared by reacting, in liquid phase, an appropriate isocyanate and S-thiocarbamoylhydrosulfamine or S-carbamoylhydrosulfamine, e.g., S-(dimethylthiocarbamoyl)-N-methylhydrosulfamine or S-(dimethylcarbamoyl)hydrosulfamine. All the compounds are useful as rubber-curing agents.

4 Claims, No Drawings

1-HYDROCARBYL-3-MONO- AND -DITHIOCARBAMOYLUREAS

BACKGROUND OF THE INVENTION

1. Field of the Invention

This invention relates to, and has as its principal object provision of, novel ureas bearing a thiocarbamoylthio or carbamoylthio substituent. Specifically, these are 1-hydrocarbyl-3-(thiocarbamoylthio) ureas and 1-hydrocarbyl-3-(carbamoylthio)ureas, a new class of compounds that finds use as rubber curing agents.

2. Prior Art

The novel ureas of this invention have not been described in the chemical literature. The closest art known is that of S. R. Richter in U.S. Pat. No. 3,276,855, which discloses compounds of the type shown by the formula:

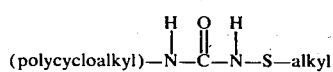

Japanese Pat. No. 12,246 shows the production of Nacylureaus of the type:

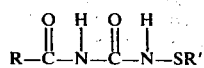

by reaction of acyl isocyanates with sulfenamides or diaminosulfides.

F. Kurzer [J. Chem. Soc., London, 549, 3360 (1953)] reports the synthesis of N-aryl-N'-arylsulfenyl ureas by the following reactions:

ArNHCONH$_2$ + Ar'SCl ⟶ ArNHCONH-S-Ar'
ArNCO + Ar'SNH$_2$ ⟶ ArNHCONH-S-Ar'.

DESCRIPTION OF THE INVENTION

The compounds of this invention are made by liquid-phase reaction of a mono- or diisocyanate with an S-thiocarbamoylsulfamine or S-carbamoylsulfamine according to one of the following two equations:

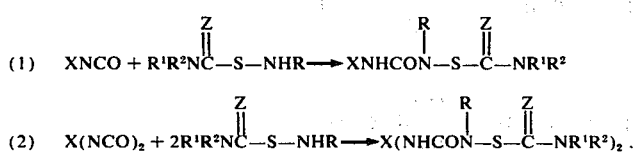

The products of the invention may be defined by the following composite formula:

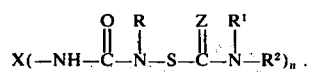

In the above equations and formulae, the following definitions hold:

Z may be S or O;

R and R$^1$, alike or different, may be hydrogen or alkyl, cycloalkyl, alkenyl, aryl, alkaryl or aralkyl hydrocarbon of up to 8 carbon atoms;

R$^2$ may be alkyl, cycloalkyl, alkenyl, aryl, alkaryl or aralkyl hydrocarbon of up to 8 carbon atoms;

R$^1$ and R$^2$, taken together (R$^1$ + R$^2$), may be (1) a chain of 4, 5 or 6 methylene groups, which chain may be substituted with a lower alkyl group, i.e., an alkyl group of 1 to 4 carbon atoms, or (2) —CH$_2$CH$_2$—O—CH$_2$—CH$_2$—;

$n$ may be 1 or 2; and

X, When $n$ = 1, may be alkyl of up to 8 carbon atoms; and

X, when $n$ = 2, may be alkylene, O— or S-interrupted alkylene, alkenylene, alkylenebis(arylene), arylenebis(alkylene), or arylene of up to 13 carbon atoms.

More specifically, R, R$^1$ and R$^2$, alike or different, may be: methyl, ethyl, n- and isopropyl, n-, iso-, sec- and t-butyl, amyl isoamyl, sec-amyl, active amyl, hexyl, 2- and 3-hexyl, 4-methyl-2-pentyl, heptyl, 2-, 3- and 4-heptyl, octyl, isooctyl, 3-methylheptyl, 3,3-dimethylhexyl; cyclopentyl, methylcyclopentyl, methylethylcyclopentyl, cyclohexyl, methylcyclohexyl, ethylcyclohexyl, dimethylcyclohexyl, cycloheptyl, cyclooctyl; allyl, α-methallyl, β-methallyl, 2- and 3-butentyl, 2- and 3-pentenyl, 2-, 3-, 4- and 5-hexenyl, 3-methyl-3-pentenyl, 6-heptenyl, 7-octenyl; phenyl, o-, m- and p-tolyl, o-, m- and p-tolyl, o-, m-and p-ethylphenyl, xylyls, i.e., 2,3-, 2,4-, 2,5-, 2,6-, 3,4- and 3,5-dimethylphenyls; benzyl, α- and β-phenylethyl.

Specific radicals within the above definitions of X include, when $n$ = 1, i.e., when derived from a monoisocyanate: methyl, ethyl, propyl, the butyls, isohexyl, heptyl, octyl and 2-ethylhexyl.

When $n$ = 2, i.e., when X is derived from a diisocyanate, X may be: trimethylene, tetramethylene, 3-methyloctamethylene, 3-methoxyheptamethylene, 3-thiapentamethylene, 4-thiaheptamethylene, 4-oxaheptamethylene, 2,2-dimethylpentamethylene, decamethylene, dodecamethylene, 3-butoxyhexamethylene, 4,9-dioxadodecamethylene, 7-thiatridecamethylene, 1,2-cyclohexylene, 1,4-cyclohexylene; butenylene; methylenebis-p-phenylene, 1,2-ethylene-bis-p-phenylene; 4,4'-methoxybiphenylene, 1,5-naphthalene, 4,4'-biphenylene; p-xylylene, p-pheny;enebis(ethyl), 1,4-naphthylenebis(methyl) or 1,5-naphthalenebis(-methyl).

In the practice of the invention, the mono- or diisocyanate are simply intimately contacted with the S-thiocarbamoylhydrosulfamine or S-carbamoylhydrosulfamine in liquid phase and the reaction allowed to proceed, usually in solution in a suitable solvent and at around ambient temperature and pressure.

A large number of isocyanates are known [see, for example, Siefken, Ann. 562, 75 (1949)] and many are articles of commerce. Monoisocyanates suitable for use in the process of the invention include: methyl, propyl, butyl and isohexyl isocyanates.

Diisocyanates include: alkylene and O- or S-interrupted alkylene such as: trimethylene diisocyanate; tetramethylene diisocyanate; 3-methyloctamethylene diisocyanate; 3-methoxyheptamethylene diisocyanate; di(2-isocyanatoethyl)sulfide; di(3-isocyanatopropyl)-sulfide; di(3-isocyanatopropyl)oxide; 2,2-dimethylpentamethylene diisocyanate; decamethylene diisocyanate; dodecamethylene diisocyanate; 3-butoxyhexamethylene diisocyanate; 4,9-dioxadecamethylene diisocyanate; di(6-isocyanatohexyl)sulfide; 1,2-di(isocyanatomethyl)cyclohexane; 1,4-di(isocyanatomethyl)cyclohexane; alkenylene such as: 1,4-diisocyanato-2-butene; alkylenebis(arylene) such as: 1,2-ethylene-bis-p-phenylene diisocyanate; arylene such as: 3,3'-methoxy-biphenylene-4,4' diisocyanate; 1,5-naphthalene diisocyanate; 4,4'-biphenylene diisocyanate; 1,2-ethylene-bis-*p*-phenylene diisocyanate; and alkylenebis(alkyl) such as *p*-xylylene diisocyanate; 1,4-bis(2-isocyanatoethyl)benzene; 1,4-bis(isocyanatomethyl)naphthalene; 1,5-bis(isocyanatomethyl)naphthalene; and 1,5-tetralin diisocyante.

The S-thiocarbamoylhydrosulfamines

are also a known class of compounds and literature references to some of them appear in the examples. They can be made by the treatment of a dithiocarbamate salt with a hydroxylamine-O-sulfonate or an N-chloroamine, or by addition of an oxidizing agent such as sodium hypochlorite or iodine to an aqueous mixture of a dithiocarbamate salt and an amine.

S-Thiocarbamoylhydrosulfamines suitable for the practice of this invention are listed in Column C of Table I, following, and may be prepared by reaction of the dithiocarbamate of Column a with the amine of Column B according to the procedure of Smith et al. [J. Org. Chem. 14, 935 (1949)].

Table I

| A | B | C |
|---|---|---|
| $(CH_3)_2NCS_2Na$ | $C_2H_5NH_2$ | $(CH_3)_2NCS_2-NHC_2H_5$ |
| $(CH_3)_2NCS_2Na$ | ⟨S⟩—NH$_2$ | $(CH_3)_2NCS_2$—NH—⟨S⟩ |
| $(n-Bu)_2NCS_2Na$ | $CH_3NH_2$ | $(n-Bu)_2NCS_2NHCH_3$ |
| $(n-Bu)CH_3NCS_2Na$ | $C_3H_7NH_2$ | $(n-Bu)CH_3NCS_2NHC_3H_7$ |
| $(n-C_3H_7)CH_3NCS_2Na$ | $C_6H_5CH_2NH_2$ | $(n-C_3H_7)CH_3NCS_2NHCH_2C_6H_5$ |
| $(C_6H_5C_2H_4)CH_3NCS_2Na$ | $C_6H_5NH_2$ | $(C_6H_5C_2H_4)CH_3NCS_2NHC_6H_5$ |
| ⟨S⟩—N(CH$_3$)CS$_2$Na | $p$-CH$_3$C$_6$H$_4$NH$_2$ | ⟨S⟩—N(CH$_3$)CS$_2$NH—$p$-C$_6$H$_4$CH$_3$ |
| $CH_3(CH_2)_3CH(C_2H_5)CH_2NCS_2Na$ | $2,4-(CH_3)_2C_6H_3NH_2$ | $CH_3(CH_2)_3CH(C_2H_5)CH_2NCS_2NH—2,4-(CH_3)_2C_6H_3$ |
| $(CH_2=CHCH_2)C_6H_5NCS_2Na$ | cyclopentyl-CH$_3$-NH$_2$ | $(CH_2=CHCH_2)C_6H_5—NCS_2NH$-cyclopentyl-CH$_3$ |
| $(CH_2=CCH_3—CH_2)_2NCS_2Na$ | $n$-octyl-NH$_2$ | $(CH_2=CCH_3—CH_2)_2NCS_2NH$-$n$-octyl |
| $(C_6H_5)—n-C_4H_9NCS_2Na$ | $C_6H_5—CH_2CH_2NH_2$ | $(C_6H_5)—n-C_4H_9NCS_2NHCH_2CH_2C_6H_5$ |
| $CH_3CH=CHCH_2NHCS_2Na$ | $C_3H_7NH_2$ | $CH_3CH=CHCH_2NHCS_2NHC_3H_7$ |
| piperidine-N—CS$_2$Na | $n$-C$_6$H$_{13}$NH$_2$ | piperidine-N—CS$_2$NH-$n$-C$_6$H$_{13}$ |
| pyrrolidine-N—CS$_2$Na | $CH_2=CHCH_2NH_2$ | pyrrolidine-N—CS$_2$NHCH$_2$CH=CH$_2$ |
| 2-methylpyrrolidine-N—CS$_2$Na | $CH_2=CH(CH_2)_4NH_2$ | 2-methylpyrrolidine-N—CS$_2$NH(CH$_2$)$_4$CH=CH$_2$ |
| hexahydroazepine-N—CS$_2$Na | $C_2H_5NH_2$ | hexahydroazepine—CS$_2$NHC$_2$H$_5$ |
| 4-methylpiperidine-N—CS$_2$Na | $CH_3CH=CHCH_2NH_2$ | 4-methylpiperidine—CS$_2$NHCH$_2$CH=CHCH$_3$ |
| morpholine-N—CS$_2$Na | $CH_2=C(CH_3)CH_2NH_2$ | morpholine-N—CS$_2$NHCH$_2$—C(CH$_3$)=CH$_2$ |
| morpholine-N—CS$_2$Na | $C_6H_5NH_2$ | morpholine-N—CS$_2$NHC$_6$H$_5$ |

S-Carbamoylhydrosulfamines

(R¹R²NCSNHR)

Suitable intermediate S-carbamoylhydrosulfamines are listed in Column C of Table II, which follows. They may be prepared by oxidation of mixtures of the thiocarbamate of Column A and the amine of Column b with sodium hypochlorite or iodine as oxidizing agent.

TABLE II

| A | B | C |
|---|---|---|
| $(CH_3)_2NCOSNa$ | $C_6H_5NH_2$ | $(CH_3)_2NCOSNHC_6H_5$ |
| $(C_2H_5)_2NCOSNa$ | $C_6H_5CH_2NH_2$ | $(C_2H_5)_2NCOSNHCH_2C_6H_5$ |
| n-octyl-NHCOSNa | $C_4H_9NH_2$ | n-octyl-NHCOSNHC$_4$H$_9$ |
| O⟨  ⟩NCOSNa (morpholine) | $CH_3(CH_2)_3CH(C_2H_5)CH_2NH_2$ | O⟨  ⟩NCOSNHCH$_2$CH(C$_2$H$_5$)(CH$_2$)$_3$CH$_3$ |
| ⟨  ⟩NCOSNa (cycloheptyl) | $CH_3NH_2$ | ⟨  ⟩NCOSNHCH$_3$ |
| ⟨ ⟩NCOSNa (cyclobutyl) | p-$CH_3C_6H_4NH_2$ | ⟨ ⟩NCOSNH-p-$C_6H_4$-CH$_3$ |
| $C_6H_5N(CH_3)COSNa$ | $C_6H_5CH_2CH_2NH_2$ | $C_6H_5(CH_3)NCOSNHCH_2CH_2C_6H_5$ |
| $C_6H_5NHCOSNa$ | $CH_2=CH-CH_2NH_2$ | $C_6H_5NHCOSNHCH_2-CH=CH_2$ |
| $[CH_2=C(CH_3)CH_2]_2NCOSNa$ | $CH_2=CH(CH_2)_4NH_2$ | $[CH_2=C(CH_3)CH_2]_2NCOSNH(CH_2)_4CH=CH_2$ |
| $CH_3$⟨  ⟩NCOSNa | $C_2H_5NH_2$ | $CH_3$⟨  ⟩NCOSNHC$_2$H$_5$ |
| $(isoamyl)_2NCOSNa$ | $CH_3NH_2$ | $(isoamyl)_2NCOS-NHCH_3$ |
| O⟨  ⟩N-COSNa | $C_6H_5NH_2$ | O⟨  ⟩N-COSNHC$_6$H$_5$ |
| $(CH_2=CHCH_2)CH_3NCOSNa$ | 3,4-$(CH_3)_2C_6H_3NH_2$ | $(CH_2=CH-CH_2)CH_3NCOS-NH-3,4-(CH_3)_2C_6H_3$ |
| p-$CH_3C_6H_4CH_2(CH_3)NCOSNa$ | $(CH_3)_2CH(CH_2)_2NH_2$ | p-$CH_3C_6H_4-CH_2(CH_3)NCOS-NH(CH_2)_2CH(CH_3)_2$ |
| $(CH_2=CHCH_2)C_6H_5NCOSNa$ | $CH_3NH_2$ | $(CH_2=CHCH_2)C_6H_5NCOSNHCH_3$ |
| $C_6H_5CH_2NHCOSNa$ | $CH_3NH_2$ | $C_6H_5CH_2NH-COSNHCH_3$ | usable in the process of the invention may be made by reaction of thiocarbamate salts with a hydroxylamine-O-sulfonate or an N-chloroamine or by addition of an oxidant such as sodium hypochlorite or iodine to an aqueous mixture of a thiocarbamate salt and an amine. They may also be prepared by reaction of amines with chlorocarbonylsulfenyl chloride.

S-Carbamoylhydrosulfamines of the type RNHCOSNHR are similarly useful in this invention. These may be prepared by the reaction of primary amines with chlorocarbonylsulfenyl chloride according to the method of Zumach and Kühle [see Zumach et al., Angew. Chem. Int. Ed. Engl., 9, 57 (1970)]. Thus, the amines of Column A of Table III, which follows, yield the S-carbamoylhydrosulfamines of Column B by reaction with chlorocarbonylsulfenyl chloride.

TABLE III

| A | B |
|---|---|
| $CH_3NH_2$ | $CH_3NHCOSNHCH_3$ |
| n-$C_3H_7NH_2$ | n-$C_3H_7NHCOSNH$-n-$C_3H_7$ |
| i-$C_3H_7NH_2$ | i-$C_3H_7NHCOSNH$-n-$C_3H_7$ |
| $C_4H_9NH_2$ | $C_4H_9NHCOSNHC_4H_9$ |
| n-octylNH$_2$ | n-octylNHCOSNH—n-octyl |
| $(CH_3)_2CHCH_2CH_2NH_2$ | $(CH_3)_2CH(CH_2)_2NHCOSNH(CH_2)_2CH(CH_3)_2$ |
| $CH_2=CHCH_2NH_2$ | $CH_2=CHCH_2NHCOSNHCH_2-CH=CH_2$ |
| $CH_2=CH(CH_2)_4NH_2$ | $CH_2=CH(CH_2)_4NHCOSNH(CH_2)_4CH=CH_2$ |
| $CH_2=C(CH_3)CH_2NH_2$ | $CH_2=C(CH_3)CH_2NHCOSNHCH_2-C(CH_3)=CH_2$ |

TABLE III-continued

| A | B |
|---|---|
| ⟨S⟩-NH₂ | ⟨S⟩-NH-COS-NH-⟨S⟩ |
| [S⟩-NH₂ | [S⟩-NH-COS-NH-⟨S] |
| []-NH₂ with CH₃ | []NHCOSNH-[] with CH₃ CH₃ |
| C₆H₅NH₂ | C₆H₅NHCOSNHC₆H₅ |
| o, m, and p-CH₃C₆H₄NH₂ | o, m and p-CH₃—C₆H₄NHCOSNH—C₆H₄—CH₃ |
| 2,4-(CH₃)₂C₆H₃NH₂ | 2,4-(CH₃)₂C₆H₃NHCOSNH—2,4-(CH₃)₂C₆H₃ |
| C₆H₅CH₂NH₂ | C₆H₅CH₂NHCOSNHCH₂C₆H₅ |
| C₆H₅CH₂CH₂NH₂ | C₆H₅CH₂CH₂NHCOSNHCH₂CH₂C₆H₅ |

Solvents suitable for use in the invention are aliphatic and aromatic hydrocarbons such as hexane, isooctane, benzene, toluene, and xylene, and their halogenated derivatives as chloroform, carbon tetrachloride, 1,1,1-trichloroethane, trichlorotrifluoroethane, and chlorobenzene, ethers and carbon disulfide. The reactants can also be contacted in melt form if desired. In large-scale preparations, however, the use of an inert solvent is advantageous to aid in control of the reaction.

For most effective utilization of materials, the reactants, are usually mixed together in molar equivalents, though an amount of the urea proportional to the reactant used in deficiency will form if the reactants are not used in 1:1 molar ratio.

The reaction is conveniently carried out at temperatures of 10° to 100°C., ambient temperature often being employed. Pressure is not critical, and ambient pressure is usually used for the sake of convenience.

The reaction proceeds in the presence or absence of catalysts. Catalysts are advantageous in enabling the use of lower temperatures and/or shorter times. The alkyltin dialkanoates, such as dibutyltin dilaurate, are suitable. Tertiary amines such as trimethylamine, triethylamine, tripropylamine, tetramethylethylenediamine, 1,4-diazabicyclo[2.2.2]octane, and pyridine are also effective catalysts.

The products are recovered by known means, such as filtration from the reaction solvent as they crystallize out, or by evaporation of the reaction solvent. The products may be purified if desired by recrystallization from known organic solvents.

EMBODIMENTS OF THE INVENTION

Specific embodiments of the invention are given in the examples which follow. Pressures and temperatures are ambient and percentages are by weight unless otherwise noted.

EXAMPLE 1

1-Ethyl-3-(dimethylthiocarbamoylthio)urea

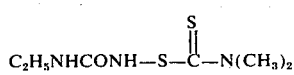

C₂H₅NHCONH—S—C(=S)—N(CH₃)₂

To 1.36 g. (0.01 mole) of S-(dimethylthiocarbamoyl)hydrosulfamine in 10 ml. of carbon tetrachloride was added 0.71 g. (0.01 mole) of ethyl isocyanate and 2 drops of dibutyltin dilaurate. After 64 hours, the urea that formed was filtered off; yield, 1.55 g. (75%). After recrystallization from dioxane, it melted at 173°–175°C.

Anal. Calcd. for C₆H₁₃N₃OS₂: C, 34.76; H, 6.32; N, 20.27. Found: C, 34.82; H, 6.68; N, 20.14.

EXAMPLE 2

Bis[3-(dimethylthiocarbamoylthio)-p-ureidophenyl[methane

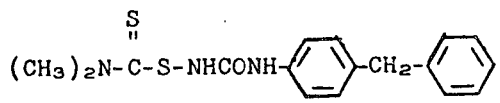

(CH₃)₂N-C(=S)-S-NHCONH-⟨⟩-CH₂-⟨⟩

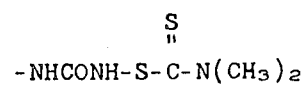

-NHCONH-S-C(=S)-N(CH₃)₂

To 5.44 g. (0.04 mole) of S-(dimethylthiocarbamoyl)hydrosulfamine in 35 ml. of carbon tetrachloride was added 5 g. (0.02 mole) of methylenebis(p-phenyl isocyanate) in 10 ml. of carbon tetrachloride and 2 drops of dibutyltin dilaurate. After 24 hours, the separated urea was filtered off and washed with dichloromethane; yield, 9.6 g. (92%); m.p. 220°C. (dec.).

EXAMPLE 3

1-Methyl-3-(dimethylcarbamoylthio)urea

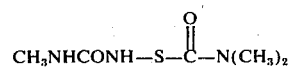

CH₃NHCONH—S—C(=O)—N(CH₃)₂

One gram (0.017 mole) of methyl isocyanate was added to 2.04 g. of S-(dimethylcarbamoyl)hydrosulfamine and 1 drop of dibutyltin dilaurate dissolved in dichloromethane. After 24 hours the 1-methyl-3-(dimethylcarbamoylthio)urea (1.91 g., 64%) was filtered off and recrystallized from dioxane; mp 157°–159°C.

Anal. Calcd. for C₅H₁₁N₃O₂S: C, 33.89; H, 6.26; N, 23.72. Found: C, 34.05; H, 6.35; N, 23.89.

The S-(dimethylcarbamoyl)hydrosulfamine required above was made by addition of a 30% aqueous solution of sodium hydroxylamine-O-sulfonate to a 30% aqueous solution of potassium dimethylthiocarbamate at 15°–20°C. The solution was filtered and extracted six times with ether. After drying with sodium sulfate, the ether was removed to leave a 90 % yield of (CH₃)₂NC(O)—S—NH₂, mp 63°–64.5°C. after recrystallization from carbon tetrachloride.

The practice of the invention is further shown by the following Table IV. When the isocyanate of Column A is reacted with the hydrosulfamine of Column B, the 1-hydrocarbyl-3-(thiocarbamoylthio)ureas or 1-hydrocarbyl-3-(carbamoylthio)ureas of Column C are obtained.

TABLE IV

| Column A | Column B |
|---|---|
| CH₃NCO | (CH₃)₂NCSSNH(CH₂)₇CH₃ |
| OCN—C₆H₄—C₆H₄—NCO | (C₄H₉)₂NCSSNH—C₆H₁₁ |
| ONC(CH₂)₆NCO | [(CH₃)₂CH]₂NCSSNH₂ |

Column C

CH₃NHCON(—(CH₂)₇CH₃)—S—C(=S)—N(CH₃)₂

(C₄H₉)₂NC(=S)—S—N(C₆H₁₁)CONH—C₆H₄—C₆H₄—NHCON(C₆H₁₁)—S—C(=S)—N(C₄H₉)₂

[(CH₃)₂CH]₂NC(=S)—S—NHCONH(CH₂)₆NHCONH—S—C(=S)—N[CH(CH₃)₂]₂

(CH₂(C₆H₄—NCO)₂)     C₆H₅—NHC(O)—S—NHC₆H₅

OCN—(CH₂)₆—NCO     C₂H₅NHC(O)—S—NHC₂H₅

C₆H₅NH—C(O)—S—N(C₆H₅)—CO—NH—C₆H₄—CH₂—C₆H₄—NH—CO—N(C₆H₅)—S—C(O)—NHC₆H₅

C₂H₅NHC(O)—S—N(C₂H₅)—C(O)—NH—(CH₂)₆—NH—C(O)—N(C₂H₅)—S—C(O)NHC₂H₅

Anal. Calcd. for C₃H₈N₂OS: C, 29.97; H, 6.71; N, 23.31. Found: C, 29.75; H, 6.72; N, 22.87.

EXAMPLE 4

Bis[3-(dimethylcarbamoylthio)-p-ureidophenyl]methane

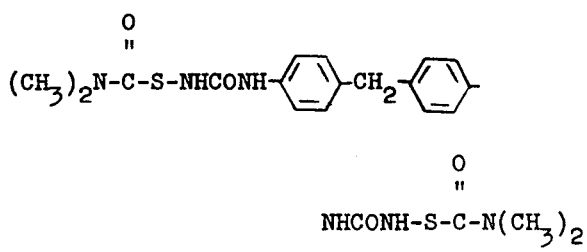

Mixing S-(dimethylcarbamoyl)hydrosulfamine and methylenebis(p-phenyl isocyanate) in tetrahydrofuran in a mole ratio of 2:1 in the presence of dibutyltin dilaurate catalyst formed the above bis-urea, mp 280°C. (dec.).

UTILITY

The compounds of this invention are useful as rubber curing agents, as illustrated by Example A (wherein parts are by weight).

EXAMPLE A

Part I

Rubber compounding was carried out on a rubber mill as follows:
 20 parts of natural rubber
 1.2 parts of zinc oxide
 0.1 part of stearic acid
 0.1 part of mercaptobenzothiazole
 1.36 part of product of Example 1

The above ingredients were milled in at 70°C. in the order given and the compound stock was cured in a mold at 140°C. for 40 minutes. Cured rubber of good elasticity and strength resulted.

Part II

A control run was carried out by repeating the procedure of Part I except that the product of Example 1 was omitted. The product was a sticky material with a tensile strength near zero.

Since obvious modifications and equivalents will be evident to those skilled in the chemical arts, I propose to be bound only by the appended claims.

The embodiments of the invention in which an exclusive property or privelege is claimed are defined as follows:

1. A compound of the formula

wherein:
Z is S or O;
R and R$^1$, alike or different, are hydrogen, or a hydrocarbon radical of up to 8 carbon atoms selected from the group consisting of alkyl, cycloalkyl, alkenyl, aryl, alkaryl, and aralkyl; and R$^2$ is a hydrocarbon radical of up to 8 carbon atoms selected from the group consisting of alkyl, cycloalkyl, alkenyl, aryl, alkaryl and aralkyl; or R$^1$ and R$^2$, taken together (R$^1$+R$^2$), are (1) a chain of 4, 5 or 6 methylene groups which chain may be substituted with an alkyl group of 1 to 4 carbon atoms, or (2) —CH$_2$CH$_2$—O—CH$_2$CH$_2$—; and
X is a radical of up to 13 carbon atoms selected from the group consisting of alkylene, O- or S-interrupted alkylene, alkenylene, alkylenebis(arylene), arylenebis(alkylene), and arylene.

2. The compound of claim 1 named bis[3-(dimethylthiocarbamoylthio)-p-ureidophenyl]methane.

3. The compound named 1-ethyl-3-(dimethylthiocarbamoylthio)urea.

4. The compound named 1-methyl-3-(dimethylcarbamoylthio)urea.

* * * * *